United States Patent
Sawada et al.

(10) Patent No.: US 9,937,271 B2
(45) Date of Patent: Apr. 10, 2018

(54) **PREVENTION OF *ESCHERICHIA COLI* DIARRHEA**

(71) Applicants: IDEMITSU KOSAN CO., LTD., Chiyoda-ku (JP); NATIONAL INSTITUTE OF ADVANCED INDUSTRIAL SCIENCE AND TECHNOLOGY, Chiyoda-ku (JP); HOKUSAN CO. LTD, Kitahiroshima-shi (JP)

(72) Inventors: Kazutoshi Sawada, Sodegaura (JP); Takeshi Matsui, Sodegaura (JP); Eiji Takita, Sodegaura (JP); Takeshi Matsumura, Sapporo (JP); Akira Ito, Sapporo (JP); Noriko Tabayashi, Kitahiroshima (JP)

(73) Assignees: IDEMITSU KOSAN CO., LTD., Chiyoda-ku (JP); NATIONAL INSTITUTE OF ADVANCED INDUSTRIAL SCIENCE AND TECHNOLOGY, Chiyoda-ku (JP); HOKUSAN CO., LTD., Kitahiroshima-shi (JP)

(*) Notice: Subject to any disclaimer, the term of this patent is extended or adjusted under 35 U.S.C. 154(b) by 0 days.

(21) Appl. No.: 15/039,628

(22) PCT Filed: Nov. 25, 2014

(86) PCT No.: PCT/JP2014/081113
§ 371 (c)(1),
(2) Date: May 26, 2016

(87) PCT Pub. No.: WO2015/080099
PCT Pub. Date: Jun. 4, 2015

(65) Prior Publication Data
US 2017/0173179 A1    Jun. 22, 2017

(30) Foreign Application Priority Data

Nov. 26, 2013   (JP) .................. 2013-244096

(51) Int. Cl.
*A61K 38/00*   (2006.01)
*A61K 48/00*   (2006.01)
*A61K 39/108*  (2006.01)

(52) U.S. Cl.
CPC ............ *A61K 48/005* (2013.01); *A61K 38/00* (2013.01); *A61K 39/0258* (2013.01)

(58) Field of Classification Search
None
See application file for complete search history.

(56) References Cited

U.S. PATENT DOCUMENTS

| | | |
|---|---|---|
| 2004/0191273 A1 | 9/2004 | Jilka |
| 2011/0002950 A1 | 1/2011 | Sawada et al. |
| 2011/0231960 A1 | 9/2011 | Sawada et al. |
| 2015/0133635 A1 | 5/2015 | Sawada et al. |
| 2017/0028046 A1 | 2/2017 | Sawada et al. |

FOREIGN PATENT DOCUMENTS

| | | |
|---|---|---|
| EP | 0 793 717 B1 | 1/2005 |
| EP | 2 169 054 A1 | 3/2010 |
| EP | 2 287 300 A1 | 2/2011 |
| EP | 3 075 388 A1 | 10/2016 |
| JP | 2011-115164 A | 6/2011 |
| WO | WO 00/75345 A1 | 12/2000 |
| WO | WO 2009/004842 A1 | 1/2009 |
| WO | WO 2009/133882 A1 | 11/2009 |

OTHER PUBLICATIONS

Johannes et al., Nature Rev. Microbiol., 8:105-116, 2010).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
International Search Report dated Mar. 3, 2015 in PCT/JP2014/081113 (with English language translation).
International Preliminary Report on Patentability and Written Opinion dated Jun. 9, 2016 in PCT/JP2014/081113 (submitting English translation only).
Yoshifumi Takeda, "Studies of Diarrheagenic Toxins Produced by *Escherichia coli*" Nippon Saikingaku Zasshi (Journal of Japanese Society for Bacteriology), vol. 54, No. 2, 1999, pp. 387-399 (with Partial English language translation).
Stephen J. Streatfield, et al., "Plant-based vaccines: unique advantages" Vaccine 19, 2001, pp. 2742-2748.
Jun Lin, et al., "Protection of piglets against enteric colibacillosis by intranasal immunization with K88ac (F4ac) fimbriae and heat labile enterotoxin of *Escherichia coli*" Veterinary Microbiology, vol. 162, 2013, pp. 731-739.
Takeshi Matsui, et al., "Production of double repeated B subunit of Shiga toxin 2e at high levels in transgenic lettuce plants as vaccine material for porcine edema disease" Transgenic Research, vol. 20, 2011, pp. 735-748.
Extended European Search Report dated Jun. 9, 2017 in Patent Application No. 14865227.4.
Toshio Sato et al., "Evaluation of Recombinant Forms of the Shiga Toxin Variant Stx2eB Subunit and Non-Toxic Mutant Stx2e as Vaccine Candidates against Porcine Edema Disease", Bacteriology, Journal of Veterinary Medical Science, vol. 75, No. 10, XP55364204, Jan. 1, 2013, pp. 1309-1315.
Thi Kim Nguyen Oanh et al., "Protection of Piglets against Edema Disease by Maternal Immunization with Stx2e Toxoid", Infection and Immunity, vol. 80, No. 1, XP55364189, Jan. 1, 2012, pp. 469-473.

(Continued)

*Primary Examiner* — Brian Gangle
(74) *Attorney, Agent, or Firm* — Oblon, McClelland, Maier & Neustadt, L.L.P.

(57) ABSTRACT

The present invention provides an agent for controlling *Escherichia coli* diarrhea comprising a Shiga toxin as an active ingredient.

11 Claims, 3 Drawing Sheets

(56) References Cited

OTHER PUBLICATIONS

Tariq A. Haq et al., "Oral Immunization with a Recombinant Bacterial Antigen Produced in Transgenic Plants", Science, American Association for the Advancement of Science, vol. 268, No. 5211, XP002024034, May 5, 1995, pp. 714-716.

* cited by examiner

PREVENTION OF ESCHERICHIA COLI DIARRHEA

TECHNICAL FIELD

The present invention relates to an agent for controlling *Escherichia coli* diarrhea comprising a Shiga toxin as an active ingredient. Further, the present invention relates to a method for producing an increased amount of a Shiga toxin controlling agent.

BACKGROUND ART

In many cases, *Escherichia coli* diarrhea is caused by enterotoxigenic *Escherichia coli*. The primary causative toxin of *Escherichia coli* diarrhea is heat-labile toxin (LT) or heat-stable toxin (ST), which a proteinaceous endotoxin produced by enterotoxigenic *Escherichia coli*. To prevent diseases caused by these bacterial toxins, a method is known in which a vaccine is administered by an injection or a transnasal spray, or administered orally.

*Escherichia coli* diarrhea is classified into diarrhea during the neonatal period (early-onset diarrhea) and diarrhea after weaning. Preventive measures for these kinds of diarrhea include administration of antibiotics and administration of vaccines. To prevent diarrhea during the neonatal period, inactivated vaccines for immunizing mother pigs have been developed. With the use of such vaccines, suckling pigs are able to receive vaccine antibodies from their mother pigs through milk. In commercially available vaccines which can be obtained domestically, colonization factors such as purified F4, F5 and F6 pili, or inactivated bacterial cells of *Escherichia coli* expressing these colonization factors are used as immunogens. Some vaccines contain the B subunit of LT, in addition to the above mentioned colonization factors, for the purpose of blocking the binding of LT to cell receptors.

For the prevention of diarrhea after weaning, on the other hand, the amount of immunoglobulin G received from mother pigs via colostrum is considered to be insufficient to protect young pigs, since the half-life of immunoglobulin G in neonatal pigs have been reported to be 13.8 days in average. Although efforts have been made to develop live vaccines which express pili or subunit vaccines comprising pili as components, none of them has been put to practical use. Further, the emergence of *Escherichia coli* has come to be known in recent years, which produces Stx2e toxin in addition to LT and ST toxins, and more integrated preventive measures are demanded.

Patent Document 1 discloses that the B subunit of Shiga toxin has a vaccine effect against edema disease of swine. Patent Document 2 describes that, when two or three each of Shiga toxin vaccines and cholera toxins are linked for the purpose of improving the production of a recombinant hybrid protein in plants, the amount of the accumulated hybrid protein can be increased. Further, Patent Document 3 discloses the oral administration of plants transformed to express heat-labile toxin and cholera toxin, to carry out immunization.

Non-patent Document 1 discloses findings that the results of experiments in mice suggest that the B subunit of heat-labile toxin may be promising in the prevention of *Escherichia coli* diarrhea. Non-patent Document 2 describes that heat-labile holotoxin including the B subunit has a vaccine effect against *Escherichia coli* diarrhea in pigs. Further, Non-patent Document 3 discloses that a hybrid protein in which the B subunits of Shiga toxin are linked can be highly expressed in lettuce.

However, edema disease of swine and *Escherichia coli* diarrhea generally require different countermeasures in terms of controlling epidemics. Besides, all of the above mentioned prior art documents are silent about the fact that Shiga toxin has an effect of controlling *Escherichia coli* diarrhea. In addition, although Patent Document 1, 2, and Non-patent Document 3 disclose that it is possible to produce hybrid proteins by introducing Shiga toxin into lettuce or tobacco, it is not described therein that if the hybrid proteins can be produced efficiently in vegetative-propagation plants such as strawberry. Moreover, there are problems that, even if Shiga toxin proteins can be highly expressed in tobacco, they are not suitable in terms of application, because the purification of the proteins and the like are required in order to develop controlling agents and the like, and that it is difficult to maintain acquired recombinant lines over generations, in the case of seed-propagation plants such as tobacco.

PRIOR ART DOCUMENTS

Patent Documents

Patent Document 1: WO 2009/004842 A
Patent Document 2: WO 2009/133882 A
Patent Document 3: EP 0793717 B

Non-Patent Documents

Non-patent Document 1: Vaccine 19 (2001) 2742-2748
Non-patent Document 2: Vet Microbiol. 2013 Mar. 23; 162(2-4): 731-9
Non-patent Document 3: Matsui et al., 2011, Transgenic Res., 20; 735-48

SUMMARY OF THE INVENTION

Problems to be Solved by the Invention

An object of the present invention is to prevent *Escherichia coli* diarrhea, more particularly, to prevent diarrhea after weaning. Another object of the present invention is to provide a method for producing a sufficient amount of a Shiga toxin protein.

Means for Solving the Problems

The present inventors have engaged in intensive studies to solve the above mentioned problems, and discovered as a result that the B subunit of Shiga toxin is effective as an agent for controlling (has a vaccine effect, immunostimulating effect, or therapeutic effect against) *Escherichia coli* diarrhea, particularly, diarrhea after weaning, and effective in preventing the infection *Escherichia coli* having multiple toxins such as LT and ST toxins.

The present inventors have thereby completed the present invention.

The present invention as follows.

(1) An agent for controlling *Escherichia coli* diarrhea, comprising a Shiga toxin as an active ingredient.
(2) The agent for controlling *Escherichia coli* diarrhea according to (1), wherein the Shiga toxin is a Shiga toxin B subunit.

(3) The agent for controlling *Escherichia coli* diarrhea according to (1) or (2), comprising a hybrid protein comprising at least two Shiga toxin proteins tandemly linked via a peptide linker, as an active ingredient.
(4) The agent for controlling *Escherichia coli* diarrhea according to any one of (1) to (3), wherein the agent is administered as a transformant transformed with a recombinant vector containing a DNA construct comprising a DNA coding for the Shiga toxin, and expressing the Shiga toxin.
(5) The agent for controlling *Escherichia coli* diarrhea according to (4), wherein the transformant is a vegetative-propagation plant.
(6) The agent for controlling *Escherichia coli* diarrhea according to (5), wherein the vegetative-propagation plant is strawberry.
(7) The agent for controlling *Escherichia coli* diarrhea according to any one of (1) to (6), for use in a non-human animal.
(8) The agent for controlling *Escherichia coli* diarrhea according to (7), wherein the non-human animal is a pig, a cow or a chicken.
(9) The agent for controlling *Escherichia coli* diarrhea according to (8), wherein the non-human animal is a pig in the lactation period or of up to 120-day old, or a mother pig.
(10) A method for producing an agent for controlling *Escherichia coli* diarrhea, the method comprising transforming a vegetative-propagation plant with a recombinant vector containing a DNA construct comprising a DNA coding for a Shiga toxin.
(11) A method for controlling *Escherichia coli* diarrhea in a non-human animal, the method comprising administering a Shiga toxin or a transformant containing the Shiga toxin to the non-human animal.
(12) An agent for improving fattening of an animal comprising a B subunit of Shiga toxin protein as an active ingredient.
(13) A Shiga toxin for use in controlling of *Escherichia coli* diarrhea in an animal.
(14) Use of a Shiga toxin for producing an agent for controlling *Escherichia coli* diarrhea in an animal.

Effect of the Invention

Since the agent for controlling *Escherichia coli* diarrhea according to the present invention functions as a preventive agent (a vaccine or immunostimulant) or a therapeutic agent, it is capable of preventing or treating *Escherichia coli* diarrhea such as diarrhea after weaning, and as a result, it is effective in improving the fattening of pigs. According to the control agent of the present invention, it is possible to prevent the infection with *Escherichia coli* having multiple toxins. Further, the control agent according to the present invention has a therapeutic effect of reducing the symptoms of *Escherichia coli* diarrhea.

Since the transformant according to the present invention is a transformant obtained by transforming a vegetative-propagation plant, both the clonal expansion of an acquired recombinant line and the maintenance of the same line can be carried out easily, making it useful in situations where the production of a large number of genetically identical seedlings is required.

EMBODIMENTS FOR CARRYING OUT THE INVENTION

Figure 1:
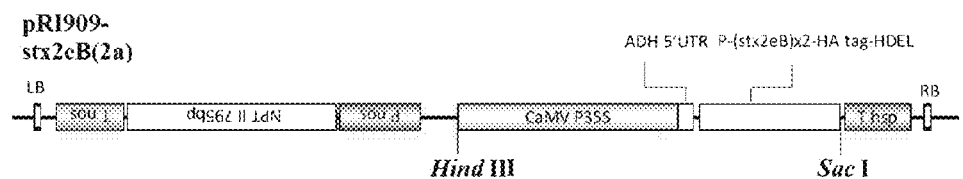
FIG. 1 is a view illustrating a modified type 2a plasmid construct obtained by introducing B subunits of Shiga toxin protein into an *Agrobacterium tumefaciens* Ti plasmid.
Figure 2:
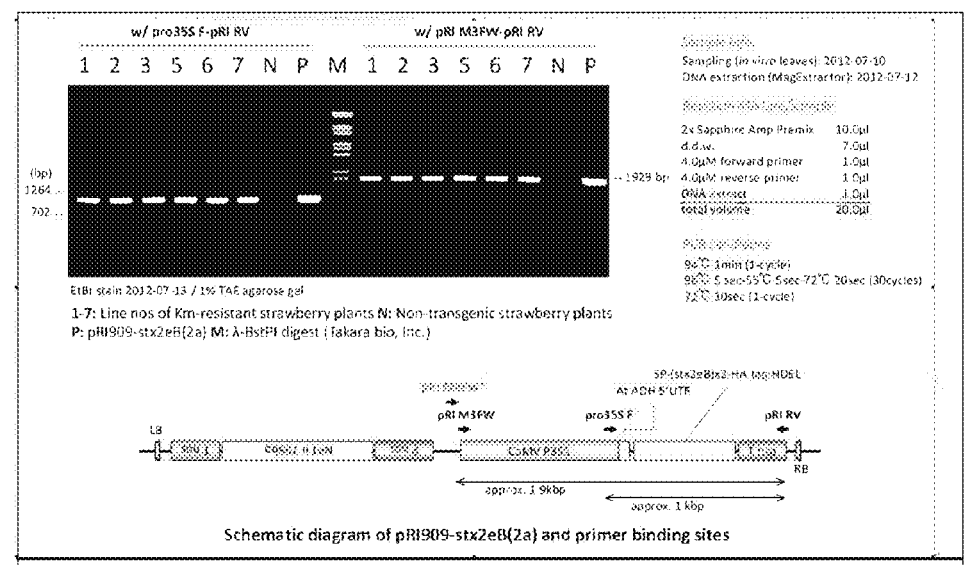
FIG. 2 illustrates the results of a PCR analysis of transformed strawberry strains with an antibiotic resistance (electrophoresis images).

The agent for controlling *Escherichia coli* diarrhea according to the present invention comprises a Shiga toxin as an active ingredient.

Shiga toxin (Stx) is classified into Type I (Stx1) and Type II (Stx2). Stx1 is further classified into subclasses a to d, and Stx2 is classified into subclasses a to g. The type of toxin produced by edema disease bacteria is Stx2e. A Shiga toxin protein is composed of one A subunit, which is the main body of the toxin, and five B subunits involved in entry into the intestinal mucosa.

Stx2e, also referred to as a "verotoxin" besides "Shiga toxin", is a holotoxin composed of one A subunit molecule, which is the main body of the toxin, and five B subunit molecules involved in the entry into the intestinal mucosa, and it has a function of inhibiting protein synthesis by acting on ribosomes in eukaryotic cells. Stx2e is a virulence factor which directly causes various types of pathological conditions such as hemorrhagic diarrhea, hemolytic-uremic syndrome (HUS), and acute encephalopathy that are observed upon infection with enterohemorrhagic *Escherichia coli* or *Shigella*.

Stx2e is also known as swine edema disease toxin, and its A subunit (Stx2eA) is represented by the amino acid sequence of SEQ ID NO: 4, and its B subunit (Stx2eB) is represented by the amino acid sequence of SEQ ID NO: 6.

Stx2eA and Stx2eB may have the amino acid sequences represented by SEQ ID NO: 4 and SEQ ID NO: 6, respectively, except that one or several amino acids are substituted, deleted, inserted and/or added, as long as they are capable of eliciting an immune response when administered to an animal such as a pig. The term "several" as used above means, for example, preferably a number of 2 to 30, more preferably 2 to 20, and still more preferably 2 to 10 in Stx2eA; and a number of preferably 2 to 10, more preferably 2 to 5, and still more preferably 2 to 3 in Stx2eB.

Further, Stx2eA and Stx2eB may be proteins having a sequence identity of preferably 85% or more, more preferably 90% or more, and still more preferably 95% or more to the amino acid sequences represented by SEQ ID NO: 4 and SEQ ID NO: 6, respectively, and capable of eliciting an immune response when administered to an animal such as a pig.

The Stx2e to be used in the present invention may be either the A subunit or the B subunit, but the B subunit is preferred.

The agent for controlling *Escherichia coli* diarrhea according to the present invention exhibits an effect of controlling *Escherichia coli* diarrhea, by comprising as an active ingredient the Shiga toxin as described above. *Escherichia coli* diarrhea is caused by an infection with enterotoxigenic *Escherichia coli* which produces either or both of heat-labile enterotoxin (LT) and heat-stable enterotoxin (ST). In acute cases, dehydration occurs rapidly to result in death within several days. Even if infected animals could recover, they may often be susceptible to pneumonia and maldevelopment, possibly resulting in considerable economic loss.

Heat-labile enterotoxin (LT) is referred to as heat-labile toxin. Heat-labile enterotoxin is a protein virtually the same as cholera toxin, and is a holotoxin composed of one A subunit molecule, which is the main body of the toxin, and five B subunit molecules. It has a molecular weight of 86,000. Heat-labile enterotoxin is considered to affect the ion transport system of a membrane by activating adenylate cyclase in mucosal epithelial cells and increasing the level of cAMP, which in turn causes an outflow of water, resulting in diarrhea. *Escherichia coli* which produces this toxin is referred to as enterotoxigenic *Escherichia coli* (ETEC).

Heat-stable enterotoxin (ST) is a heat-stable toxin consisting of a peptide having a molecular weight of 2,000. Heat-stable enterotoxin affects the ion transport system of the membrane by activating adenylate cyclase in the mucosal epithelial cells and increasing the level of cAMP, which in turn causes an outflow of water, resulting in diarrhea. *Escherichia coli* which produces this toxin is referred to as enterotoxigenic *Escherichia coli* (ETEC).

Surprisingly, the agent for controlling *Escherichia coli* diarrhea according to the present invention is effective in preventing the infection with *Escherichia coli* having multiple toxins such as LT and ST toxins.

The controlling agent according to the present invention has a therapeutic effect of reducing the symptoms of *Escherichia coli* diarrhea in humans and animals.

In a preferred embodiment, the agent for controlling *Escherichia coli* diarrhea according to the present invention is a hybrid protein in which at least two B subunits of Shiga toxin protein are tandemly linked via a peptide linker.

In the present specification, the term "agent for controlling *Escherichia coli* diarrhea" may be used to generally refer to: an agent for controlling *Escherichia coli* diarrhea and an agent for improving fattening, comprising as an active ingredient the Shiga toxin or the hybrid protein; a DNA construct coding for the Shiga toxin or the hybrid protein; a plant transformed with a vector containing the DNA construct coding for the Shiga toxin or the hybrid protein. The agent for controlling *Escherichia coli* diarrhea according to the present invention may be in the form of a pharmaceutical such as a vaccine or an immunostimulant, or in the form of a feed, as long as it comprises the above mentioned Shiga toxin or the hybrid protein. In the present invention, the term "controlling" includes both prevention and treatment.

The peptide linker to be used in the present invention preferably has from 12 to 25, and more preferably from 12 to 22 amino acids. Further, the peptide linker to be used in the present invention preferably has a proline content of from 20 to 27%, and more preferably; from 20 to 25%.

Prolines are preferably arranged with an interval of two or three amino acids in the peptide linker. However, even in the above mentioned arrangement, five or less, preferably four or less amino acids other than proline may be arranged consecutively, at the terminus of the peptide. Such a preferred peptide linker is disclosed, for example, in WO 2009/133882 A.

In the present invention, the peptide linker is preferably a peptide (PG12) having the amino acid sequence represented by SEQ ID NO: 2. Alternatively, the peptide linker may be a peptide having a sequence identity of 90% or more, preferably 95% or more, to the above mentioned sequence.

In the hybrid protein to be used in the present invention, it is preferred that two or more B subunits be tandemly linked via the above mentioned peptide. In the hybrid protein to be used in the present invention, it is more preferred that the two B subunits be tandemly linked via PG12 (SEQ ID NO: 2). The hybrid protein to be used in the present invention may include an A subunit, and when it does, the A subunit is preferably detoxified.

Further, it is preferred that the above mentioned peptide linker be further added to the C terminus of the hybrid protein to be used in the present invention. In particular, it is preferred that PG12 be added to the C terminus of the hybrid protein to be used in the present invention.

The hybrid protein to be used in the present invention has, for example, the amino acid sequence represented by SEQ ID NO: 8. In the hybrid protein having the amino acid sequence represented by SEQ ID NO: 8, two Stx2eBs are tandemly linked via PG1.2, and another PG12 is further added to its C terminus.

By using a peptide such as the PG12 as a linker for linking the Shiga toxin proteins, the level of the Shiga toxin protein accumulated in plant cells will be increased.

In the hybrid protein to be used in the present invention, a secretory signal peptide derived from a plant, and/or a chloroplast transit signal peptide is preferably added to its amino terminus. The term "added" as used herein is a concept including both the case where the secretory signal peptide is directly bound to the amino terminus of the two or more Shiga toxin proteins linked via the above mentioned peptide, and the case where the secretory signal peptide is bound thereto via another peptide.

The secretory signal peptide is preferably derived from a plant belonging to the family Solanaceae, Brassicaceae, or Asteraceae, more preferably, derived from a plant belonging to the genus *Nicotiana, Arabidopsis, Lactuca* or the like, and still more preferably derived from tobacco (*Nicotiana tabacum*), *Arabidopsis thaliana*, lettuce (*Lactuca saliva*) or the like.

Further, the secretory signal peptide is preferably derived from β-D-glucan exohydrolase of *Nicotiana tabacum* or 38k-Da peroxidase of *Nicotiana tabacum* (GenBank Accession D 42064). The secretory signal peptide may be, for example, a peptide derived from die β-D-glucan exohydrolase of *Nicotiana tabacum* and having the amino acid sequence represented by SEQ ID NO: 10. The nucleotide sequence of a DNA which codes for the β-D-glucan exohydrolase of *Nicotiana tabacum* is represented, for example, by the sequence of SEQ ID NO: 9.

Preferred chloroplast transit signal peptides are described, for example, in WO 2009/004842 A and WO 2009/133882 A.

In the hybrid protein to be used in the present invention, a signal peptide such as an endoplasmic reticulum retention signal peptide or a vacuolar transport signal peptide may be added to its carboxyl terminus. The term "added" as used herein is a concept including both the case where the signal peptide is directly bound to the carboxyl terminus of the hybrid protein, and the case where the signal peptide is bound thereto via another peptide. In the present specification, a hybrid protein in which the secretory signal peptide is added to its amino terminus and the endoplasmic reticulum retention signal peptide is added to its carboxyl terminus is also referred to as an endoplasmic reticulum-type (ER) hybrid protein, and a DNA construct coding for the endoplasmic reticulum-type hybrid protein is referred to as an endoplasmic reticulum-type DNA construct. Many studies have reported that the endoplasmic reticulum-type hybrid protein is efficiently accumulated in eukaryotes.

In the hybrid protein to be used in the present invention, it is preferred that the endoplasmic reticulum retention signal peptide be added to its carboxyl terminus. Preferred endoplasmic reticulum retention signal peptides are disclosed, for example, in WO 2009/004842 A and WO 2009/133882 A. Among these, HDEL sequence (SEQ ID NO: 11) can be used.

Other preferred vacuolar transport signal peptides are disclosed, for example in WO 2009/004842 A and WO 2009/133882 A.

The hybrid protein to be used in the present invention can be synthesized chemically, or can be produced by genetic engineering. A method for producing the hybrid protein by genetic engineering will be described later.

The DNA construct to be used in the present invention is characterized by comprising a DNA coding for the above mentioned hybrid protein.

In other words, the DNA construct to be used in the present invention includes a DNA in which two or more DNAs each coding for the Shiga toxin protein are tandemly linked via a DNA coding for the above mentioned peptide. The DNA coding for the peptide linker is represented, for example, by SEQ ID NO: 1 (PG12). Examples of the DNA coding for the Shiga toxin protein include a DNA (SEQ ID NO: 3) coding for Stx2eA and a DNA (SEQ ID NO: 5) coding for Stx2eB. The DNA coding for the peptide and the DNAs coding for the Shiga toxin proteins are linked in-frame, excluding stop codons.

The DNA coding for the Shiga toxin protein can be obtained by a common genetic engineering technique based on the nucleotide sequence of SEQ ID NO: 3 or 5, for example. Specifically, a cDNA library is prepared from a bacterium which produces each Shiga toxin according to a conventional method, and a desired clone is selected from the library using a probe prepared based on the above mentioned nucleotide sequence. Alternatively, the DNA can also be synthesized chemically, based on the nucleotide sequence, or synthesized by PCR using genomic DNA as a template, and 5'- and 3'-terminal nucleotide sequences of the above mentioned sequence as primers.

The DNA coding for the hybrid protein to be used in the present invention is represented, for example, by SEQ ID NO: 7.

In the DNA coding for the hybrid protein, it is also preferred that a codon(s) corresponding to an amino acid(s) constituting the hybrid protein be modified as appropriate such that the amount of the translated hybrid protein is increased, depending on the host cell in which the hybrid protein is produced.

The modification of the codon(s) can be carried out, for example, by referring to a method disclosed by Kang et al., (2004). Further, examples of the modification method include a method for selecting a codon(s) frequently used in the host cell, a method for selecting a codon(s) having a high GC content, and a method for selecting a codon(s) frequently used in housekeeping genes in the host cell.

The DNA coding for the hybrid protein may also be a DNA which hybridizes with the DNA having the nucleotide sequence of SEQ ID NO: 7 under stringent conditions. The term "stringent conditions" refers to the conditions in which a so-called specific hybrid is formed, but not a non-specific hybrid. Examples of the stringent conditions include those in which two DNAs having a high sequence identity to one another, preferably two DNAs having a sequence identity of 80% or more, more preferably 90% or more, and particularly preferably 95% or more to one another are hybridized with each other, but two DNAs having a sequence identity lower than that described above are not hybridized. The conditions may be, for example: 2×SSC (330 mM NaCl, 30 mM citric acid) at 42° C.; and preferably: 0.1×SSC (330 mM NaCl, 30 mM citric acid) at 60° C.

In the DNA construct to be used in the present invention, it is preferred that the DNA coding for the hybrid protein be operably-linked to an enhancer. The term "operably" as used herein means that, when the DNA construct to be used in the present invention is inserted into a vector including a suitable promoter, and the vector is introduced into a suitable host cell, the hybrid protein is produced in die host cell. Further, the term "linked" refers to both the case in which two DNAs are directly linked and the case in which two DNAs are linked via another nucleotide sequence. Examples of the enhancer include Kozak sequence and a 5'-untranslated region of an alcohol dehydrogenase gene derived from a plant. Particularly preferably, the DNA coding for the hybrid protein is operably-linked to the 5'-untranslated region of an alcohol dehydrogenase gene derived from a plant.

The 5'-untranslated region of an alcohol dehydrogenase gene refers to a region including a nucleotide sequence from the transcription start site before the translation start site (ATG, methionine), of a gene coding for the alcohol dehydrogenase. This region has a function to increase the translation level. The phrase "function to increase the translation level" refers to a function to increase the amount of a protein produced by translation when the information encoded in a structural gene is transcribed and then translated to produce the protein. The above mentioned region may be a region derived from a plant. It is preferably derived from a plant belonging to the family Solanaceae, Brassicaceae, or Asteraceae, more preferably, derived from a plant belonging to the genus *Nicotiana, Arabidopsis, Lactuca* or the like, and still ore preferably derived from tobacco (*Nicotiana tabacum*), *Arabidopsis thaliana*, lettuce (*Lactuca saliva*) or the like. The 5'-untranslated region of an alcohol dehydrogenase gene may be, for example, the 5'-untranslated region of an alcohol dehydrogenase gene (NtADH 5'UTR) (SEQ ID NO: 12) derived from tobacco *Nicotiana tabacum*). By using the NtADH 5'UTR region in which three nucleotides upstream of the translation start site are modified (NtADHmod 5'UTR) (SEQ ID NO: 13), in particular, a higher translation can be expected.

A method for obtaining the 5'-untranslated region of an alcohol dehydrogenase gene derived from a plant is described, for example, in WO 2009/133882 A.

In the nucleotide sequence of the NtADHmod 5'UTR such as one represented by SEQ ID NO: 13, one or several nucleotides may be substituted, deleted, inserted and/or added, as long as its function to increase the translation level is maintained. The term "several" as used above means, preferably a number of from 2 to 10, more preferably from 2 to 5, and particularly preferably from 2 to 3.

In addition, a DNA having a sequence identity of preferably 85% or more, and particularly preferably 90% or more to the NtADHmod 5'UTR and having a function to increase the translation level may also be used.

It is possible to determine whether the above mentioned region has an intended function to increase the translation level or not, for example, by a transient assay using a GUS (β-glucuronidase) gene or luciferase gene as a reporter gene in tobacco cultured cells, or an assay in transformed cells engineered to carry those genes in a chromosome.

The DNA construct to be used in the present invention has, for example, the nucleotide sequence represented by SEQ ID NO: 14.

The DNA construct having the nucleotide sequence represented by SEQ ID NO: 14 is a DNA construct in which the DNA coding for the hybrid protein in which two Stx2eB proteins are tandemly linked via PG12, the secretory signal peptide is added to its amino terminus, and the endoplasmic reticulum retention signal peptide is added to its carboxyl terminus, is linked to the NtADHmod 5'UTR.

Such a DNA construct as described above is preferably 2BH plasmid shown in FIG. 4, in Matsui et al., 2011, Transgenic Res., 20; 735-48.

The DNA construct to be used in the present invention can be prepared by a common genetic engineering technique, which includes the following procedures: digesting each of the DNAs such as the 5'-untranslated region of an alcohol dehydrogenase gene derived from a plant, a DNA coding for the secretory signal peptide derived from a plant, the DNA coding for the Shiga toxin protein, and a DNA coding for the endoplasmic reticulum retention signal peptide with a suitable restriction enzyme; and linking the resulting fragments with a suitable ligase.

The recombinant vector to be used in the present invention comprises the above mentioned DNA construct. The recombinant vector to be used in the present invention may be any vector in which the DNA coding for the hybrid protein is inserted into the vector such that the DNA can be expressed in a host cell into which the vector is introduced. The vector is not particularly limited as long as it can be replicated in a host cell, and examples thereof include a plasmid DNA, a viral DNA and the like. Further, it is preferred that the vector include a selective marker such as a drug resistance gene. The plasmid DNA can be prepared from *Escherichia coli* or *Agrobacterium tumefaciens* by the alkaline extraction method (Birnboim, H. C. & Doly, J. (1979) Nucleic acid Res 7: 1513) or a variation thereof. Commercially available plasmids such as pBI221, pBI121, pBI101, pIG121Hm and the like can also be used. As the viral DNA, pTB2 (Donson et al., 1991) and the like can be used, for example (see, Donson J., Kerney C M., Hilf M E., Dawson W O. Systemic expression of a bacterial gene by a tobacco mosaic virus-based vector. Proc. Natl. Acad. Sci. (1991) 88: 7204-7208).

A promoter to be used in the vector can be selected as appropriate depending on the type of host cell into which the vector is introduced. A preferred promoter may be, for example, a cauliflower mosaic virus 35S RNA promoter (Odell. et al. 1985 Nature 313:810), a rice actin promoter (Zhang et al. 1991 Plant Cell 3:1155), a corn ubiquitin promoter (Cornejo et al. 1993 Plant Mol. Biol. 23:567), or the like. Further, a terminator to be used in the vector may also be selected as appropriate depending on the type of host cell into which the vector is introduced. A preferred terminator may be, for example, a nopaline synthase gene transcription terminator, a cauliflower mosaic virus 35S RNA terminator, or the like.

The recombinant vector to be used in the present invention can be prepared, for example as follows.

First, the above mentioned DNA construct is digested with a suitable restriction enzyme, or a restriction enzyme site is added to the DNA construct by PCR. Subsequently, the resulting DNA construct is inserted into the restriction enzyme site or multicloning site of a vector.

The transformant to be used in the present invention is characterized by being transformed with the above mentioned recombinant vector. The host cells to be used for the transformation may be eukaryotic cells or prokaryotic cells.

The eukaryotic cells are preferably plant cells, and among these, particularly preferred are cells of plants belonging to the family Asteraceae (including those belonging to the genus *Lactuca*, for example), Solanaceae, Brassicaceae, and Chenopodiaceae. In the present invention, cells of plants belonging to the family Rosaceae, particularly, cells of plants belonging to the genus *Fragaria* are preferably used. Preferably, strawberry (*Fragaria×ananassa*) used. Examples of the cultivar of strawberry include Toyonoka, Nyoho, Summer berry, HS-138 and the like.

When strawberry cells are used as host cells, a recombinant vector such as one including the cauliflower mosaic virus 35S RNA promoter or the like can be used as the vector.

The prokaryotic cells may be cells of *Escherichia coli*, *Agrobacterium tumefaciens* or the like.

The transformant to be used in the present invention can be prepared by introducing the vector according to the present invention into host cells using a common genetic engineering technique. Examples of the method which can be used to introduce the vector include: a method using *Agrobacterium* (Hood, et al., 1993, Transgenic, Res. 2: 218, Hiei, et al., 1994 Plant J. 6: 271), an electroporation method (Tada, et al., 1990, Theor. Appl. Genet, 80:475), a polyethylene glycol method (Lazzeri, et al., 1991, Theor. Appl. Genet. 81:437), a particle gun method (Sanford, et al., 1987, J. Part. Sci. tech. 5:27), a polycation method (Ohtsuki), and the like.

After introducing the vector to be used in the present invention into the host cells, the transformant according to the present invention can be selected based on the phenotype of the selective marker. Further, the Shiga toxin protein can be produced by culturing the selected transformant. The culture medium and conditions to be used in the culture can be selected as appropriate, depending on the type of the transformant.

When plant cells are used as the host cells, culture of selected plant cells in accordance with a conventional method allows for regenerating a plant body, and for accumulating a sufficient amount of the Shiga toxin protein inside the plant cells or outside the cell membrane of the plant cells. The method varies depending on the type of plant cells to be used, and examples thereof include the method of Visser et al. (Theor. Appl. Genet 78:594 (1989)) for potato cells, and the method of Nagata and Takebe (Planta 99:12 (1971)) for tobacco cells.

*Agrobacterium tumefaciens* infects a plant through a wound in the plant, and carries a large extrachromosomal element referred to as a Ti (tumor-inducing) plasmid. Many laboratories have devoted considerable effort over several years to develop an *Agrobacterium* system, and as a result, it has become possible to transform various types of plant tissues as desired. Examples of representative tissues transformed by the above mentioned technique include tissues of: tobacco, tomato, sunflower, cotton, rapeseed, potato, poplar, soybean and the like.

It has been demonstrated that various species of plants can be regenerated from tissues transformed with *Agrobacterium tumefaciens*. Examples of such plants include sunflower, tomato, white clover, rapeseed, cotton, tobacco, potato, corn, rice, and many other kinds of vegetable crops.

In the present invention, a vegetative-propagation plant such as the above mentioned strawberry and potato is preferably transformed with an *Agrobacterium tumefaciens* Ti vector. Further, in the present invention, it is preferred that a sufficient amount of the Shiga toxin protein be produced, in the case of strawberry, in the entire plant body of the strawberry including its leaves and fruits. In the case of potato, it is preferred that a sufficient amount of the Shiga toxin protein be produced in the entire plant body of the potato including its leaves, stems, and tubers.

The agent for controlling *Escherichia coli* diarrhea according to the present invention may include the above mentioned transformant. The agent for controlling *Escherichia coli* diarrhea according to the present invention may include the entire or a part of the transformant containing the Stx2e protein. Further, the transformant can be used as it is, or it can be dried, crushed, and/or the like before being used. It is also possible to add an adjuvant which enhances the immunogenicity of the Stx2e protein to the agent for controlling *Escherichia coli* diarrhea according to the present invention. In general, aluminum hydroxide or the like is used as an adjuvant, in view of safety. On the other hand, since the B subunit of the Stx2e protein itself has an activity as an adjuvant, a high immunogenicity can be obtained without additionally adding an adjuvant, when the above mentioned DNA construct comprises a DNA coding for the B subunit.

The method for controlling *Escherichia coli* diarrhea according to the present invention is characterized by administering a plant body transformed with the above mentioned DNA construct to an animal. Examples of subjects to be administered with the agent for controlling *Escherichia coli* diarrhea according to the present invention include a human, pig, cow, chicken or the like. Preferably, the agent is administered to a pig.

In the case of administration to a pig, the immunization by the agent for controlling *Escherichia coli* diarrhea is carried out on a young pig in the lactation period or of up to 120-day old, preferably on a young pig in the lactation period or of up to 90-day old. Further, the immunization is preferably carried out on a mother pig during, before and after the reproductive period. Examples of the method for carrying out the immunization include a method in which a plant body transformed with the DNA construct is administered to a mother pig, and milk containing antibodies produced by the mother pig is fed to a young pig; a method in which a plant body transformed with the DNA construct is administered to a young pig in the lactation period or of up to 120-day old, preferably a young pig in the lactation period or of up to 90-day old, to directly immunize the young pig; and the like.

Examples of the method for administering the agent for controlling *Escherichia coli* diarrhea according to the present invention to a pig include a method in which a plant body transformed with the DNA construct, or a dried product or a ground product thereof, is mixed with a feed to be fed to a pig; a method in which the agent s administered to a pig by nasal drops; and the like. The dose of the agent in this case is preferably 1.5 mg or more, more preferably, 3.0 mg or more per day, in terms of the mass of the Stx2e protein. It is preferred that the agent for controlling *Escherichia coli* diarrhea according to the present invention be administered for a plurality of times at certain intervals. For example; the agent may be administered every four to seven days for a total of two to three times.

Examples of the present invention will now be described. However, the present invention is not limited by the following Examples.

EXAMPLES

Example 1

Construction of Stx2eB Expression Vector

A Stx2eB expression vector was prepared according to the method described in the section of Materials and methods in Matsui et al., 2011, Transgenic Res., 20; 735-48.

Specifically, a Stx2eB (1×2eB) in which a PG12 spacer (SEQ ID NO: 1), a HA tag and a HDEL sequence were added to its C terminus was prepared, and another Stx2eB was tandemly linked to the resultant via a PG12 spacer to form a 2×2eB. The resultant (SEQ ID NO: 14) was inserted into a binary vector pRI909 for producing a stable transformant. Such a vector is 2BH plasmid which is shown in FIG. 4 in Matsui et al., 2011, Transgenic Res., 20; 735-48.

The thus prepared binary vector is shown in FIG. 1.

Example 2

Gene Transfer Test into Strawberry

The Stx2e expression plasmid (FIG. 1) is introduced into *Agrobacterium tumefaciens* (lines EHA105 and LB4404) by a direct introduction method. The resulting kanamycin (Km)-resistant strains (in which the introduction of the plasmid had been confirmed) were used to carry out the transformation test of strawberry (cultivar: HS-138). Callus induction and redifferentiation were carried out using a Km-added medium, and antibiotic (Km)-resistant individuals were selected.

One hundred or more antibiotic-resistant individuals were obtained in each of the tests using the respective *Agrobacterium tumefaciens* lines. The confirmation of the introduced Stx2eB gene and the expression analysis of the protein were carried out, starting from those growing faster than others.

Genomic DNAs were extracted from 18 individuals of the antibiotic-resistant strains, followed by PCR analysis. The primers were used in two combinations of: pRI M3FW (SEQ ID NO: 15) and pRI RV (SEQ ID NO: 16) (fragment length to be amplified: about 1.9 kbp); and pro35SF (SEQ ID NO: 17) and pRI RV (SEQ ID NO: 16) (fragment length to be amplified: about 1 kbp); shown in FIG. 2, and the introduction of the target gene was confirmed in 17 individuals. No non-specific band was observed in either of the combinations.

Example 3

Expression Analysis of Transformed Strawberry

It was assumed from the result of the PCR analysis shown in FIG. 2 that the target gene had been inserted into the resulting redifferentiated individuals in most of the strains. Therefore, the expression analysis of the target protein was carried out in all of the lines.

About 200 to 300 mg fresh weight of leaves were sampled from the cultured strains of strawberry, and stored at −80° C. until the extraction of proteins was performed. To the above mentioned sample, a buffer (0.2 M Tris-Cl (pH=8.0), 0.1 M NaCl., 0.01 M EDTA, 0.014 M 2ME, 0.001 M PMSF, 0.05% Tween 20) was added in an amount five times the amount of the sample, and the resultant was ground in a mortar with liquid nitrogen, followed by the extraction of soluble proteins. To the thus obtained sample of soluble proteins, an equal amount of Laemmli Sample buffer (containing 5% 2-Mercaptoethanol) was added, and the resultant was subjected to heat treatment, followed by acrylamide gel electrophoresis (gel concentration: 15% , Wako). After the electrophoresis, proteins separated on the gel were transferred to a PVDF membrane, followed by Western blotting. In the Western blot analysis, a hybridoma culture supernatant, Rat 37C mAb, P-12 was diluted 1,000-fold and used as a primary antibody, and Anti-Rat IgG (whole molecule)-Peroxidase, antibody produced in rabbit (SIGMA A5795)

was diluted 12,000-fold and used as a secondary antibody. Can Get Signal solution (TOYOBO) was used for an antibody reaction, ECL plus Western Blotting Detection System (GE Healthcare) was used for a detection reaction, and the detection of chemiluminescence was carried out using VersaDoc Model 5000 (BioRad).

Figure 3:
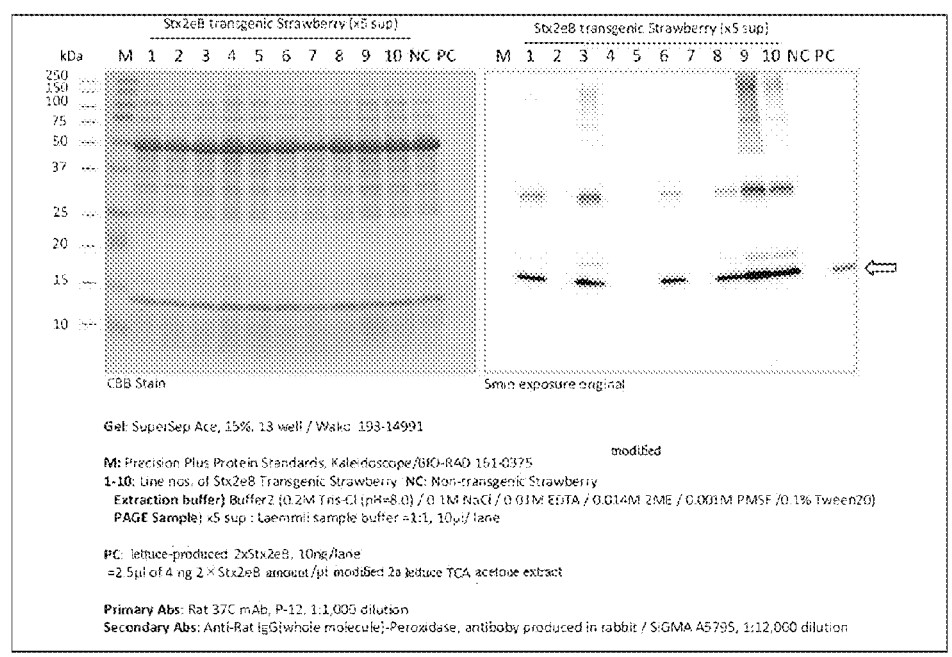
FIG. 3 illustrates the results of an expression analysis of Stx2eB protein in the transformed strawberry strains (electrophoresis images).

A part of the results is shown in FIG. 3. The expression of the target protein was confirmed in 99 lines out of 150 lines analyzed.

Example 4

Hydroponic Cultivation and Collection of Fruits

The lines in which the expression of the target protein had been confirmed were acclimated, and grown hydroponically in a closed plant factory. Thinning out of leaves, replacement of nutrient solution and the like were carried out to control the culture conditions, flowering was confirmed, and fruits were collected.

Example 5

Preparation of Sample for Administration to Pigs

The fruits were used for the preparation of the sample for administration. First, the quantification of Stx2eB contained in the fruits was carried out. The extraction of proteins was carried out in accordance with the TCA-acetone method (Shultz et, al., 2005). To a 2 ml microtube, about 10 mg of freeze-dried powder of the strawberry fruits, stainless steel beads having a diameter of 5 mm, and about 0.7 ml of TCA-acetone (10% trichloroacetic acid, 90% acetone, 0.07% 2-mercaptoethanol) cooled to $-20°$ C. were added. Then the microtube was set to TissueLyser Adapter Set 2×24 (Qiagen) which had been cooled with liquid nitrogen, and reciprocal shaking was carried out at 20 times/sec for three minutes using TissueLyser II (Qiagen), to mix the sample. After leaving the resultant to stand at $-20°$ C. for one hour, centrifugation was carried out at 16,000×g at $4°$ C. for 30 minutes to remove the supernatant, and precipitates containing proteins were obtained. Further, in order to remove impurities, about 0.7 ml of acetone/BME (100% acetone, 0.07% 2-mercaptoethanol) was added. The resultant was mixed in the same manner as described above, and centrifuged at 16,000×g at $4°$ C. for 10 minutes to remove the supernatant. The above described operation for removing impurities was repeated two more times. The resulting precipitates were dried under reduced pressure, and suspended in 1.1 ml of extraction I buffer [20 mM tris(hydroxymethyl)aminomethane (Tris)-HCl, pH 7.9, 0.5 M sodium chloride, 5 mM imidazole, 6 M urea]. The resulting suspension was centrifuged at 16,000×g at $4°$ C. for 10 minutes, and the supernatant was collected, to obtain a protein solution.

The protein solution was mixed with the same amount of sample buffer for SDS-PAGE (Ez Apply, manufactured by ATTO), and the resultant was heated for 10 minutes in boiling water to denature the proteins. The denatured proteins were diluted as appropriate, and electrophoresis (SDS-PAGE) was carried out at a constant voltage of 200 V for 40 minutes, using Criterion Cell (electrophoresis tank, BIO-RAD), Ez Run (electrophoresis buffer, ATTO), and Criterion TGX-gel (BIO-RAD). After the electrophoresis, the blotting of the gel was carried out using a Trans-Blot transfer pack (BIO RAD) and Trans-Blot Turbo (BIO RAD).

The transferred membrane was immersed in a blocking solution (TBS-based, pH 7.2, Nakalai Tesque, Inc.), and shaken at room temperature for one hour, or left to stand at $4°$ C. for 16 hours, to carry out blocking treatment. The blocked membrane was then shaken in TBS-T (137 mM sodium chloride, 2.68 mM potassium chloride, 1% polyoxyethylene sorbitan monolaurate, 25 mM Tris-HCl, pH 7.4) at room temperature for five minutes, and the shaking was repeated for a total of three times to carry out washing. A rat anti-Stx2eB monoclonal antibody, Rat 37C mAb, P-12, diluted 1,000-fold with TBS-T was used as a primary antibody in the detection of 2×Stx2eB protein by Western analysis. The membrane was immersed in the thus obtained liquid of the primary antibody, followed by shaking at room temperature for two hours to allow an antigen-antibody reaction to proceed. The membrane was then shaken in TBS-T at room temperature for five minutes, and the shaking was repeated for a total of three times to carry out washing. Anti-Rabbit IgG, AP-linked Antibody (Cell Signaling TECHNOLOGY) diluted 10,000-fold with TBS-T was used as a second antibody. The membrane was immersed in the diluted liquid, followed by shaking at room temperature for one hour to allow an antigen-antibody reaction to proceed. The membrane was then shaken in TBS-T at room temperature for five minutes, and the shaking was repeated for a total of three times to carry out washing. To carry out a chromogenic reaction with alkaline phosphatase, the washed membrane was immersed in a chromogenic solution (0.1 M sodium chloride, 5 mM chlorinated magnesium. 0.33 mg/ml nitro blue tetrazolium, 0.33 mg/ml 5-bromo-4-chloro-3-indolyl-phosphoric acid, 0.1 M Tris-HCl, pH 9.5), followed by shaking at room temperature for seven minutes. The membrane was then washed with distilled water and dried at normal temperature. The stained membrane was imaged using a scanner (PM-A900, Epson), and the quantification of the 2×Stx2eB protein was carried out using an image analysis software (CS Analyzer ver. 3.0, ATTO).

Based on the result of the above mentioned quantification, a powder of strawberry fruits to be used as the sample for administration was prepared, such that the dose of Stx2eB per animal per administration would be 1.5 mg. The powder of strawberry fruits was prepared by weighing the appropriate amount of strawberry fruits, crushing them with a mixer mill to liquefy, followed by freeze drying.

Example 6

Pig Challenge Test with Enterotoxigenic *Escherichia Coli*

(a) Bacterial Strain

*Escherichia coli* (ETEC) No. 4242-1 which produces heat-labile toxin (LT)- or heat-stable toxin (ST) isolated from a pig (obtained by Shokukaken Inc) (derived from pig deceased in outdoor field) was used in the test. Properties of the bacterial strain are as follows.

Hemolytic property: +
Pilus type: F18: −; K88: +
Toxins: Stx2e: −; ST: +; LT: +

(b) Preparation of Challenge Bacteria (Prepared Before Use)

The above mentioned bacterial strain No. 4242-1 was cultured in a IS broth medium at $37°$ C. until the logarithmic growth phase was reached. After the culture, a centrifugal separation was carried out, and bacterial cells were collected as precipitates. The bacterial cells were prepared with an alkaline Hanks' buffer, such that the dose thereof would be $2\times10^9$ CFU/animal.

(c) Administration of the Test Substance and Challenge Bacteria

Six young pigs in the weaning period, derived from one healthy mother pig reared in a hog farm, were selected. At 24-day old, the pigs were moved to an indoor facility, and divided into two groups of three as shown in Table 1. The pigs in respective groups were reared in separate spaces (pens) surrounded by fences. For the young pigs in Group 1, the test substance in a predetermined amount as shown in Table 1 (per one administration) was mixed to the feed, and voluntary oral administration was carried out at 28-day old and 31-day old. For the young pigs in Group 2, a strawberry powder which does not include the active ingredient was administered, in the same amount and the same manner as the test substance administered to Group 1. Forced oral administration of the challenge bacteria was carried out to each of the young pigs in both groups, one day after the respective administrations of the test substance, twice at 29-day old and 32-day old. The administration of the challenge bacteria was carried out by forced oral administration using a stomach catheter. Standard feed for young pigs in late artificial milk-period (manufactured by Nippon Formula Feed Manufacturing Co., Ltd.) was used, and pigs were allowed free access to feed and water. During the rearing period, the body weight of each of the pigs was recorded.

TABLE 1

| test group | test substance | administration of the challenge bacteria | number of heads |
|---|---|---|---|
| Group 1 | administration (28-day old, 31-day old) | administration (29-day old, 32-day old) | 3 |
| Group 2 | no administration | administration (29-day old, 32-day old) | 3 |

Clinical observation was carried out every day from day 0 (the day the second forced administration of the challenge bacteria was carried out) up to day 14. The observation was carried out for the items such as sparse fur and stool properties, which items are described in Manual for pathological diagnosis (Byosei Kantei Manual) and known as clinical symptoms of *Escherichia coli* diarrhea. The clinical symptom scores were determined based on the following standards.

Sparse fur (0: no, 1: yes)
Stool properties (0: normal, 1: loose stool, 2: caddy stool, 3: watery/mucous and blood stool)

Further, presence or absence of lesions (ascites) observed at autopsy was also examined.

Ascites (0: not mal, 1: mild, 2: severe)

In addition, the measurement of body weight was performed on day 5, day 10 and day 14.

(d) Test Results

Clinical Observations

The total clinical symptom scores and lesion scores at autopsy obtained for the respective items are shown in Table 2. The results revealed that it was possible to reduce the symptoms of *Escherichia coli* diarrhea in the pigs in Group 1 administered with the test substance, over the entire period of observation (from day 0 to day 14)

TABLE 2

Clinical symptom scores (left) and lesion scores at autopsy (right)

| | stool properties | sparse fur | total | Ascites | total |
|---|---|---|---|---|---|
| administered group (Group 1) | 0 | 0 | 0 | 1 | 1 |
| Control group (Group 2) | 2 | 10 | 12 | 4 | 4 |

In the young pigs in Group 2 not administered with the test substance, sparse fur began to be observed from day 10, and it was observed in all the pigs on day 14. In contrast, sparse fur was observed in none of the young pigs in Group 1 administered with the test substance. Loose stool was observed in one of the young pigs in Group 2 not administered with the test substance, starting from day 13. No abnormalities in the stool properties were observed in the young pigs in Group 1 administered with the test substance.

Changes in Body Weight

Figure 4:
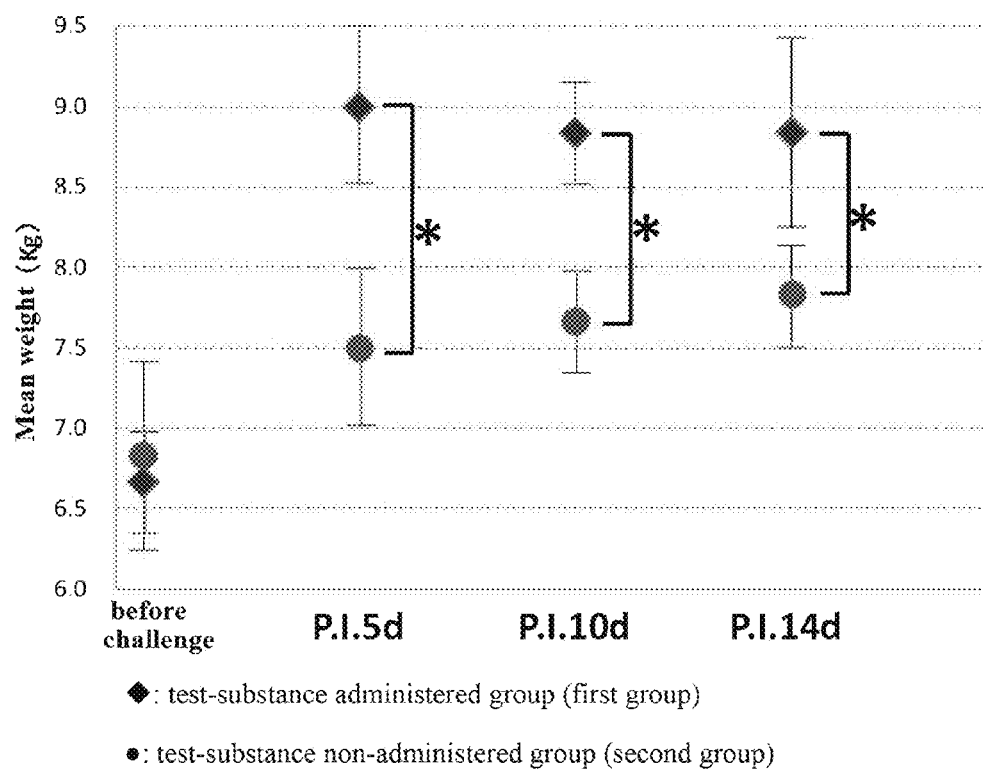
FIG. 4 is a graph illustrating the changes in body weight in pigs after challenges with enterotoxigenic *Escherichia coli*.

The changes in the body weight of the pigs over the entire test period are shown in FIG. 4.

On day 5 post challenge, the average body weight of the pigs in Group 1 was 9.0 kg. In contrast, the average body weight of the pigs in Group 2 was 7.5 kg. The difference in the body weight between the two groups was determined to be statistically significant. This tendency continued to be observed on day 10 and day 14.

Further, marked ascites was observed in two pigs in the group not administered with the test substance (Group 2), as findings at autopsy. No ascites was observed in the pigs in the group administered with the test substance (Group 1).

INDUSTRIAL APPLICABILITY

The agent for controlling *Escherichia coli* diarrhea according to the present invention is useful in the field of livestock farming.

The invention claimed is:

1. A method for controlling *Escherichia coli* diarrhea. in a pig infected with the *Escherichia coli*, the method comprising administering a Shiga toxin or a transformant containing the Shiga toxin to the pig in need thereof, wherein the Shiga toxin is a hybrid protein comprising two Shiga toxin B subunit proteins (Stx2eB) tandemly linked via a peptide linker, and wherein the *Escherichia coli* produces heat-labile toxin (LT) and/or heat-stable toxin (ST) but does not produce Stx2e toxin.

2. The method according to claim 1, wherein the Shiga toxin is administered as a transformant which is transformed with a recombinant vector containing a DNA construct comprising a DNA coding for the hybrid protein, and expresses the hybrid protein.

3. The method according to claim 1, wherein the hybrid protein is administered as a transformant which is transformed with a recombinant vector containing a DNA construct comprising a DNA coding for the hybrid protein, and expresses the hybrid protein.

4. The method according to claim 2, wherein the transformant is a vegetative-propagation plant.

5. The method according to claim 4, wherein the vegetative-propagation plant s strawberry.

6. The method according to claim 1, wherein the pig is a pig in the lactation period or of up to 120-day old, or a mother pig.

7. A method of improving fattening of a pig infected with a toxin-producing *Escherichia coli*, comprising administering a Shiga toxin as an active ingredient to the pig in need thereof, wherein said Shiga toxin protein is a hybrid protein comprising two Shiga toxin B subunit proteins (Stx2eB) tandemly linked via a peptide linker, and wherein said *Escherichia coli* produces heat-labile toxin (LT) and/or heat-stable toxin (ST) but does not produce Stx2e toxin.

8. The method according to claim 7, wherein the Shiga toxin is administered as a transformant which is transformed with a recombinant vector containing a DNA construct comprising a DNA coding for the hybrid protein, and expresses the hybrid protein.

9. The method according to claim 7, wherein the Shiga toxin is administered as a transformant which is transformed with a recombinant vector containing a DNA construct comprising a DNA coding for a hybrid protein comprising the hybrid protein, and expresses the hybrid protein.

10. The method according to claim 8, wherein the transformant is a vegetative-propagation plant.

11. The method according to claim 10, wherein the vegetative-propagation plant is strawberry.

* * * * *

SEQUENCE LISTING

<160> NUMBER OF SEQ ID NOS: 17

<210> SEQ ID NO 1
<211> LENGTH: 36
<212> TYPE: DNA
<213> ORGANISM: Artificial Sequence
<220> FEATURE:
<223> OTHER INFORMATION: an artificially synthesized DNA

<400> SEQUENCE: 1
agatcccctg gttctggtcc tggttctcct agatcc                    36

<210> SEQ ID NO 2
<211> LENGTH: 12
<212> TYPE: PRT
<213> ORGANISM: Artificial Sequence
<220> FEATURE:
<223> OTHER INFORMATION: an artificially synthesized peptide

<400> SEQUENCE: 2

Arg Ser Pro Gly Ser Gly Pro Gly Ser Pro Arg Ser
1               5                   10

<210> SEQ ID NO 3
<211> LENGTH: 959
<212> TYPE: DNA
<213> ORGANISM: Escherichia coli

<400> SEQUENCE: 3

```
atgaagtgta tattgttaaa gtggatactg tgtctgttac tgggtttttc ttcggtatcc    60
tattcccagg agtttacgat agacttttcg actcaacaaa gttatgtatc ttcgttaaat   120
agtatacgga cagcgatatc gacccctctt gaacatatat ctcagggagc tacatcggta   180
tccgttatta atcatacacc accaggaagt tatatttccg taggtatacg agggcttgat   240
gtttatcagg agcgttttga ccatcttcgt ctgattatta acgaaataa tttatatgtg   300
gctggatttg ttaatacgac aacaaatact ttctacagat tttcagattt gcacatatat   360
cattgcccgg tgtgacaact atttccatga caacggacag cagttatacc actctgcaac   420
gtgtcgcagc gctggaacgt tccggaatgc aaatcagtcg tcactcactg gtttcatcat   480
atctggcgtt aatggagttc agtggtaata caatgaccag agatgcatca agagcagttc   540
tgcgttttgt cactgtcaca gcagaagcct tacggttcag gcaaatacag agagaatttc   600
gtctggcact gtctgaaact gctcctgttt atacgatgac gccggaagac gtggacctca   660
ctctgaactg ggggagaatc agcaatgtgc ttccggagta tcggggagag gctggtgtca   720
gagtggggag aatatccttt aataatatat cagcgatact tggtactgtg ccgttatac   780
tgaattgcca tcatcagggc gcacgttctg ttcgcgccgt gaatgaagag agtcaaccag   840
aatgtcagat aactggcgac aggcccgtta taaaaataaa caatacatta tgggaaagta   900
atacagcagc agcgtttctg aacagaaagt cacagccttt atatacaact ggtgaatga   959
```

<210> SEQ ID NO 4
<211> LENGTH: 304
<212> TYPE: PRT
<213> ORGANISM: Escherichia coli

<400> SEQUENCE: 4

Met Lys Cys Ile Leu Leu Lys Trp Ile Leu Cys Leu Leu Leu Gly Phe
1               5                   10                  15

Ser Ser Val Ser Tyr Ser Gln Glu Phe Thr Ile Asp Phe Ser Thr Gln
            20                  25                  30

Gln Ser Tyr Val Ser Ser Leu Asn Ser Ala Ile Ser Thr Pro Leu Glu
        35                  40                  45

His Ile Ser Gln Gly Ala Thr Ser Val Ser Val Ile Asn His Thr Pro
    50                  55                  60

Pro Gly Ser Tyr Ile Ser Val Gly Ile Arg Gly Leu Asp Val Tyr Gln
65                  70                  75                  80

Glu Arg Phe Asp His Leu Arg Leu Ile Ile Glu Arg Asn Asn Leu Tyr
                85                  90                  95

Phe Val Asn Thr Thr Thr Asn Thr Phe Tyr Arg Phe Ser Asp Phe Ala

```
                    100                 105                 110
His Ile Ser Leu Pro Gly Val Thr Thr Ile Ser Met Thr Thr Asp Ser
            115                 120                 125

Ser Tyr Thr Thr Leu Gln Arg Val Ala Ala Leu Glu Arg Ser Gly Met
            130                 135                 140

Gln Ile Ser Arg His Ser Leu Tyr Leu Ala Leu Met Glu Phe Ser Gly
145                 150                 155                 160

Asn Thr Met Thr Arg Asp Ala Ser Arg Ala Val Leu Arg Phe Val Thr
                165                 170                 175

Val Thr Ala Glu Ala Leu Arg Phe Arg Gln Ile Gln Arg Glu Phe Arg
            180                 185                 190

Leu Ala Leu Ser Glu Thr Ala Pro Val Tyr Thr Met Thr Pro Asp Leu
            195                 200                 205

Thr Leu Asn Trp Gly Arg Ile Ser Asn Val Leu Pro Glu Tyr Arg Gly
            210                 215                 220

Glu Ala Gly Val Arg Val Gly Arg Ile Ser Phe Asn Asn Ile Ser Ala
225                 230                 235                 240

Ile Leu Gly Thr Val Ala Val Ile Leu Asn Cys His His Gln Gly Ala
                245                 250                 255

Arg Ser Val Arg Ala Glu Ser Gln Pro Glu Cys Gln Ile Thr Gly Asp
            260                 265                 270

Arg Pro Val Ile Lys Ile Asn Asn Thr Leu Trp Glu Ser Asn Thr Ala
            275                 280                 285

Ala Ala Phe Leu Asn Arg Lys Ser Gln Pro Leu Tyr Thr Thr Gly Glu
            290                 295                 300
```

<210> SEQ ID NO 5
<211> LENGTH: 210
<212> TYPE: DNA
<213> ORGANISM: Escherichia coli

<400> SEQUENCE: 5

```
gcggcggact gcgcgaaggg caagatcgag ttctcgaagt acaacgagga caacacgttc      60
acggtcaagg tctcgggccg cgagtactgg acgaaccgct ggaacctgca gccgctgctg     120
cagtcggcgc agctgacggg catgacggtc acgatcatct cgaacacgtg ctcgtcgggc     180
tcgggcttcg cgcaggtcaa gttcaactga                                      210
```

<210> SEQ ID NO 6
<211> LENGTH: 69
<212> TYPE: PRT
<213> ORGANISM: Escherichia coli

<400> SEQUENCE: 6

```
Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
            35                  40                  45

Thr Val Thr Ile Ile Ser Asn Thr Cys Ser Ser Gly Ser Gly Phe Ala
        50                  55                  60

Gln Val Lys Phe Asn
65
```

<210> SEQ ID NO 7

<211> LENGTH: 453
<212> TYPE: DNA
<213> ORGANISM: Artificial Sequence
<220> FEATURE:
<223> OTHER INFORMATION: an artificially synthesized DNA construct

<400> SEQUENCE: 7

```
gcggcggact gcgcgaaggg caagatcgag ttctcgaagt acaacgagga caacacgttc      60
acggtcaagg tctcgggccg cgagtactgg acgaaccgct ggaacctgca gccgctgctg     120
cagtcggcgc agctgacggg catgacggtc acgatcatct cgaacacgtg ctcgtcgggc     180
tcgggcttcg cgcaggtcaa gttcaacaga tcccctggtt ctggtcctgg ttctcctaga     240
tccgcggcgg actgcgcgaa gggcaagatc gagttctcga agtacaacga ggacaacacg     300
ttcacggtca aggtctcggg ccgcgagtac tggacgaacc gctggaacct gcagccgctg     360
ctgcagtcgg cgcagctgac gggcatgacg gtcacgatca tctcgaacac gtgctcgtcg     420
ggctcgggct cgcgcaggt caagttcaac tga                                   453
```

<210> SEQ ID NO 8
<211> LENGTH: 162
<212> TYPE: PRT
<213> ORGANISM: Artificial Sequence
<220> FEATURE:
<223> OTHER INFORMATION: an artificially synthesized protein

<400> SEQUENCE: 8

```
Ala Ala Asp Cys Ala Lys Gly Lys Ile Glu Phe Ser Lys Tyr Asn Glu
  1               5                  10                  15

Asp Asn Thr Phe Thr Val Lys Val Ser Gly Arg Glu Tyr Trp Thr Asn
             20                  25                  30

Arg Trp Asn Leu Gln Pro Leu Leu Gln Ser Ala Gln Leu Thr Gly Met
         35                  40                  45

Thr Val Thr Ile Ile Ser Asn Thr Cys Ser Ser Gly Ser Gly Phe Ala
     50                  55                  60

Gln Val Lys Phe Asn Arg Ser Pro Gly Ser Gly Pro Gly Ser Pro Arg
 65                  70                  75                  80

Ser Ala Ala Asp Cys Ala Lys Gly Lys Ile Glu Phe Ser Lys Tyr Asn
                 85                  90                  95

Glu Asp Asn Thr Phe Thr Val Lys Val Ser Gly Arg Glu Tyr Trp Thr
            100                 105                 110

Asn Arg Trp Asn Leu Gln Pro Leu Leu Gln Ser Ala Gln Leu Thr Gly
        115                 120                 125

Met Thr Val Thr Ile Ile Ser Asn Thr Cys Ser Ser Gly Ser Gly Phe
    130                 135                 140

Ala Gln Val Lys Phe Asn Arg Ser Pro Gly Ser Gly Pro Gly Ser Pro
145                 150                 155                 160

Arg Ser
```

<210> SEQ ID NO 9
<211> LENGTH: 72
<212> TYPE: DNA
<213> ORGANISM: Nicotiana tabacum

<400> SEQUENCE: 9

```
atggggagaa tgtcaatacc catgatgggt tttgtggtgt tatgtctatg ggcagtggta      60
gcagaaggat cc                                                          72
```

```
<210> SEQ ID NO 10
<211> LENGTH: 24
<212> TYPE: PRT
<213> ORGANISM: Nicotiana tabacum

<400> SEQUENCE: 10

Met Gly Arg Met Ser Ile Pro Met Met Gly Phe Val Val Leu Cys Leu
1               5                   10                  15

Trp Ala Val Val Ala Glu Gly Ser
            20

<210> SEQ ID NO 11
<211> LENGTH: 4
<212> TYPE: PRT
<213> ORGANISM: Artificial Sequence
<220> FEATURE:
<223> OTHER INFORMATION: an artificially synthesized peptide

<400> SEQUENCE: 11

His Asp Glu Leu
1

<210> SEQ ID NO 12
<211> LENGTH: 91
<212> TYPE: DNA
<213> ORGANISM: Nicotiana tabacum

<400> SEQUENCE: 12
tatttaactc agtattcaga acaacaaaa gttcttctct acataaaatt ttcctatttt      60
agtgatcagt gaaggaaatc aagaaaaata a                                   91

<210> SEQ ID NO 13
<211> LENGTH: 91
<212> TYPE: DNA
<213> ORGANISM: Nicotiana tabacum

<400> SEQUENCE: 13
tatttaactc agtattcaga acaacaaaa gttcttctct acataaaatt ttcctatttt      60
agtgatcagt gaaggaaatc aagaaaaaaa g                                   91

<210> SEQ ID NO 14
<211> LENGTH: 670
<212> TYPE: DNA
<213> ORGANISM: Artificial Sequence
<220> FEATURE:
<223> OTHER INFORMATION: an artificially synthesized DNA construct

<400> SEQUENCE: 14
tatttaactc agtattcaga acaacaaaa gttcttctct acataaaatt ttcctatttt      60
agtgatcagt gaaggaaatc aagaaaaaaa gatggggaga atgtcaatac ccatgatggg   120
ttttgtggtg ttatgtctat gggcagtggt agcagaagga ggatccgcgg cggactgcgc   180
gaagggcaag atcgagttct cgaagtacaa cgaggacaac acgttcacgg tcaaggtctc   240
gggccgcgag tactggacga accgctggaa cctgcagccg ctgctgcagt cggcgcagct   300
gacgggcatg acggtcacga tcatctcgaa cacgtgctcg tcgggctcgg gcttcgcgca   360
ggtcaagttc aacagatccc ctggttctgg tcctggttct cctagatccg cggcggactg   420
cgcgaagggc aagatcgagt tctcgaagta caacgaggac aacacgttca cggtcaaggt   480
ctcgggccgc gagtactgga cgaaccgctg gaacctgcag ccgctgctgc agtcggcgca   540
gctgacgggc atgacggtca cgatcatctc gaacacgtgc tcgtcgggct cgggcttcgc   600
```

```
gcaggtcaag ttcaacagat cccctggttc tggtcctggt tctcctagat ctgaacatga    660
tgaattgtga                                                          670
```

```
<210> SEQ ID NO 15
<211> LENGTH: 17
<212> TYPE: DNA
<213> ORGANISM: Artificial Sequence
<220> FEATURE:
<223> OTHER INFORMATION: an artificially synthesized primer

<400> SEQUENCE: 15
gttttcccag tcacgac                                                   17

<210> SEQ ID NO 16
<211> LENGTH: 17
<212> TYPE: DNA
<213> ORGANISM: Artificial Sequence
<220> FEATURE:
<223> OTHER INFORMATION: an artificially synthesized primer

<400> SEQUENCE: 16
caggaaacag ctatgac                                                   17

<210> SEQ ID NO 17
<211> LENGTH: 20
<212> TYPE: DNA
<213> ORGANISM: Artificial Sequence
<220> FEATURE:
<223> OTHER INFORMATION: an artificially synthesized primer

<400> SEQUENCE: 17
caatcccact atccttcgca                                                20
```